United States Patent [19]

Meggyesy

[11] 4,152,787

[45] May 8, 1979

[54] PROSTHETIC KNEE JOINT HAVING WEIGHT RESPONSIVE BRAKE

[76] Inventor: Joseph Meggyesy, 8103 Crenshaw Blvd., Inglewood, Calif. 90305

[21] Appl. No.: 814,295

[22] Filed: Jul. 11, 1977

[51] Int. Cl.² .................... A61F 1/08; F16D 55/24
[52] U.S. Cl. ........................................ 3/27; 188/71.4; 188/72.7
[58] Field of Search ................ 3/27, 26, 28, 2; 188/71.4, 72.7

[56] References Cited

U.S. PATENT DOCUMENTS

| | | | |
|---|---|---|---|
| 1,246,590 | 11/1917 | Hanger, Jr. | 3/28 |
| 2,450,728 | 10/1948 | Havens | 3/27 |
| 2,533,008 | 12/1950 | Hanson | 3/27 X |
| 2,551,537 | 5/1951 | Havens | 3/27 |
| 2,808,129 | 10/1957 | Kraus | 188/71 A |
| 2,863,684 | 12/1958 | Carroll | 3/28 X |
| 3,309,715 | 3/1967 | Nader et al. | 3/27 |
| 3,662,864 | 5/1972 | Evans | 188/72.7 X |
| 3,666,299 | 5/1972 | Butler | 3/27 X |
| 3,678,517 | 7/1972 | Ehbrecht | 3/27 |
| 3,871,779 | 3/1975 | Butler | 3/28 X |

FOREIGN PATENT DOCUMENTS

| | | | |
|---|---|---|---|
| 1099570 | 3/1955 | France | 3/27 |
| 336757 | 10/1930 | United Kingdom | 3/28 |

*Primary Examiner*—Clifford D. Crowder
*Attorney, Agent, or Firm*—J. B. McGuire

[57] ABSTRACT

A knee joint which locks when the weight of an amputee is imposed upon the prosthesis, such as when taking a step. The joint includes a housing which is rotatably mounted relative to a shaft. A plurality of metal discs are mounted on the shaft so as to be axially moveable but non-rotatable relative thereto. Interleafed with the metal plates, a plurality of fiber discs may be mounted so as to be both rotatable and axially moveable relative to the shaft, but fixed against rotation relative to the housing. A pair of wedge-shaped reaction discs may be mounted on the shaft at approximately the center of the housing. A double-wedge-shaped actuating disc may be mounted between the two reaction discs for radial movement relative to the shaft. An actuator rod connected to the stump-receiving portion of the prosthesis presses against the actuator when the amputee puts weight on the prosthesis. This causes the interleafed discs to engage in friction contact to prevent rotation of the housing and the shaft.

3 Claims, 15 Drawing Figures

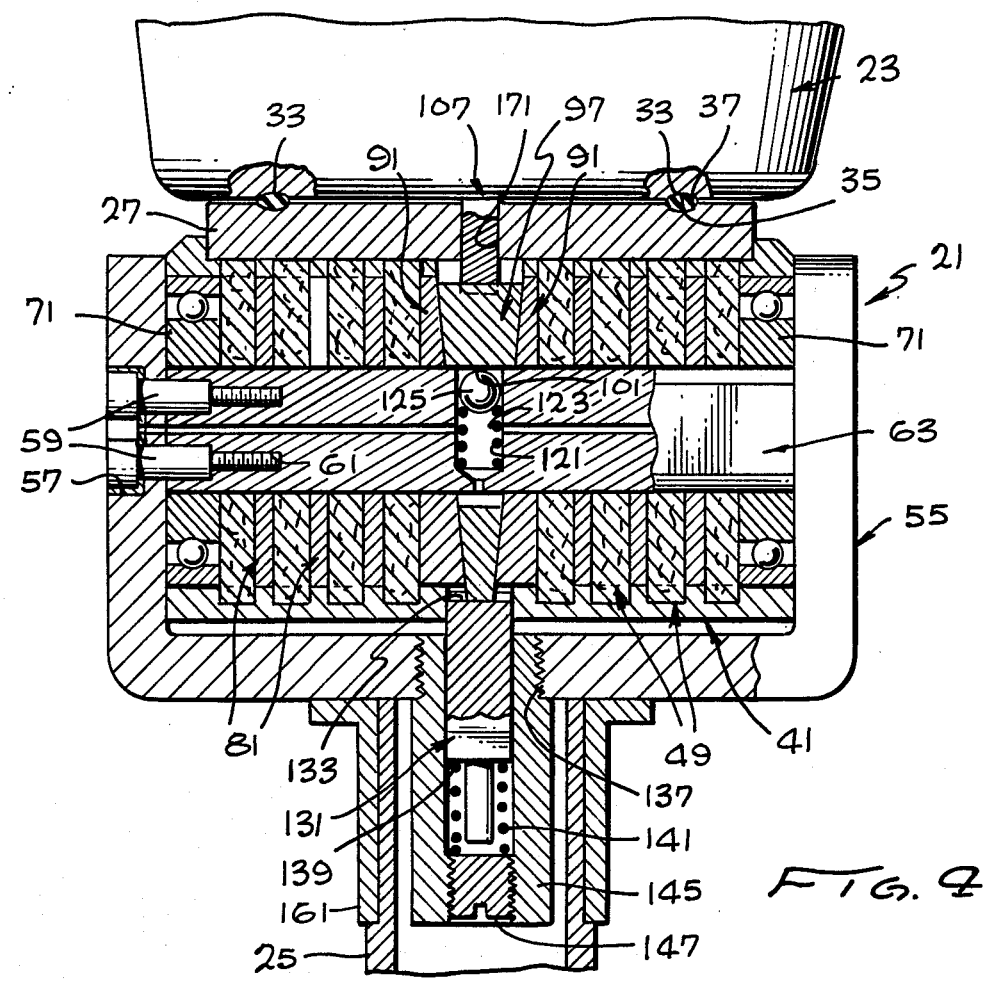
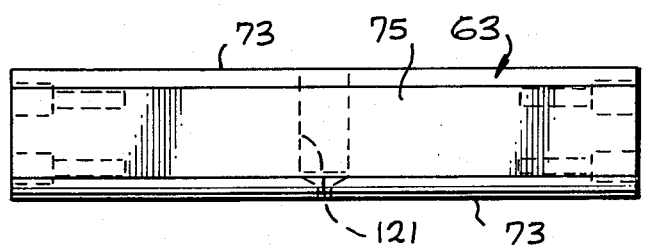
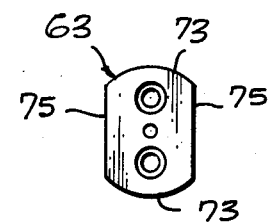

PROSTHETIC KNEE JOINT HAVING WEIGHT RESPONSIVE BRAKE

BACKGROUND OF THE INVENTION

During the last few decades, great advances have been made in the construction of prostheses which can be worn by amputees or persons suffering from birth defects in order to allow them to live as normal a life as possible. This is particularly true with respect to leg prostheses and, to a large extent, has resulted from efforts to reduce, as far as possible, the physical incapacity of soldiers injured in combat.

In order to provide as much freedom of movement as possible, a leg prosthesis which is to be worn by a person who has undergone an above-the-knee amputation normally includes a joint which allows flexion, at least to some extent. Flexion is the bending of the knee which, for example, allows the human leg to bend during an activity such as walking.

Prior art prostheses which have included such knee joints have been found to be unsatisfactory in some instances because the knee joint must be capable of allowing at least some flexion, while also being capable of being locked against flexion when the amputee puts his weight on the prosthesis, e.g., when he takes a step. Unfortunately, many presently available prostheses do not allow such freedom of movement. For example, it has been found that some prior art units do not allow the wearer to take as normal a step as possible because the knee joint fails to lock at the proper time. If locking should not occur while the amputee is walking, for example, it is quite likely that the wearer will fall, suffering physical and/or emotional injury. Consequently, it has become desirable to produce a knee joint which allows a considerable degree of flexion, while still allowing the wearer to positively lock the joint against flexion when he takes a step or otherwise puts his weight on it.

SUMMARY OF THE INVENTION

The present invention relates to a leg prosthesis, and more specifically to the knee joint which may be employed in such a prosthesis to serve the needs of an above-the-knee amputee. As presently envisioned, the invention may include a knee joint formed as a brake which may be selectively actuated, e.g., by providing structure for actuating the brake whenever an actuation force is imposed upon the amputation stump-receiving element of the prosthesis.

In the presently preferred embodiment, the brake may comprise a substantially cylindrical housing through which a shaft may extend in substantially coaxially relationship. The interior of the housing may be provided with any suitable means, such as longitudinally oriented, spline-like recesses which may be used as rotation-prevention means, as will be presently described.

The shaft may be similarly provided with rotation-prevention means which, as presently envisioned, may comprise a pair of longitudinally oriented, opposed "flats" or surfaces on the shaft. A plurality of washer-like discs may be coaxially mounted on the shaft. Every other disc may be provided with an internal bore or opening which closely cooperates with the shaft periphery, thus allowing those discs to be moved axially along the shaft, while prohibiting them from being rotated relative to the shaft. In other words, if the shaft should rotate about its axis, those discs will rotate with it.

In the interspaces between the washer-like discs, a second plurality of disks may be installed, each having one or more radial extensions thereon which fit within the splines on the inner wall of the housing. Thus, these latter discs may be prevented from rotating relative to the housing but, if their central bores or openings are formed so as to be circular, their movement may be both axial and rotational, relative to the central shaft.

Preferably, one set of discs may be constructed of metal, while the other set of discs may be formed of a suitable brake fiber. Consequently, when adjacent discs are compacted or forced into surface-to-surface abutment with one another, the friction generated by contact between adjacent discs will prevent relative rotation between them. On the other hand, when the axial force which moves the discs into such contact is released, adjacent discs may slip relative to one another to allow rotation between the housing and the shaft.

Near the axial center of the housing, structure may be provided to impose an axially directed force on the brake discs. In the preferred embodiment, this actuation structure may include a central disc formed as a double-faced wedge. On either side of the central disc, a single-faced wedge disc may be installed. The central aperture of the center disc may be formed so as to allow radial movement thereof, i.e., generally perpendicular to the shaft axis. Consequently, when the double-faced disc is moved diametrically, its wedge faces will cooperate with the wedge faces on the adjacent discs, exerting an axial pressure upon all of the discs, thereby generating movement-prohibiting friction between adjacent disc surfaces.

The central disc may, if desired, be actuated by a pin or bar connected to the stump-receiving cup which may be movably mounted relative to the knee joint housing. Thus, when the amputee puts weight on the cup, the actuating bar will move into the housing, actuating the center disc, diametrically, thereby causing the joint to lock as previously described.

If desired, means may be provided to bias the center disc in the opposite diametric direction, thereby allowing a release of the friction contact when the actuator bar is withdrawn from the housing.

Also if desired, the knee joint may be provided with any suitable means to allow the total prosthesis to be developed in as realistic a manner as possible, i.e., the addition of a plastic housing on, above, and/or below the joint. This may be provided in order to allow the total prosthesis to resemble a normal human leg as much as possible.

When reading the following detailed description and studying the accompanying drawings, those skilled in the art should bear in mind that the embodiment of the present invention set forth here is only that which is presently preferred. On the other hand, the invention which is included within this preferred embodiment shall be considered to be limited only by the claims.

BRIEF DESCRIPTION OF THE DRAWINGS

FIG. 4 comprises a sectional view of the knee joint, taken along a line IV—IV of FIG. 2, but with the joint locked;

FIG. 11 comprises the side elevation of a pivot shaft which may be employed with the present invention;

FIG. 12 comprises an end view of the shaft shown in FIG. 11;

DETAILED DESCRIPTION

Figure 1:
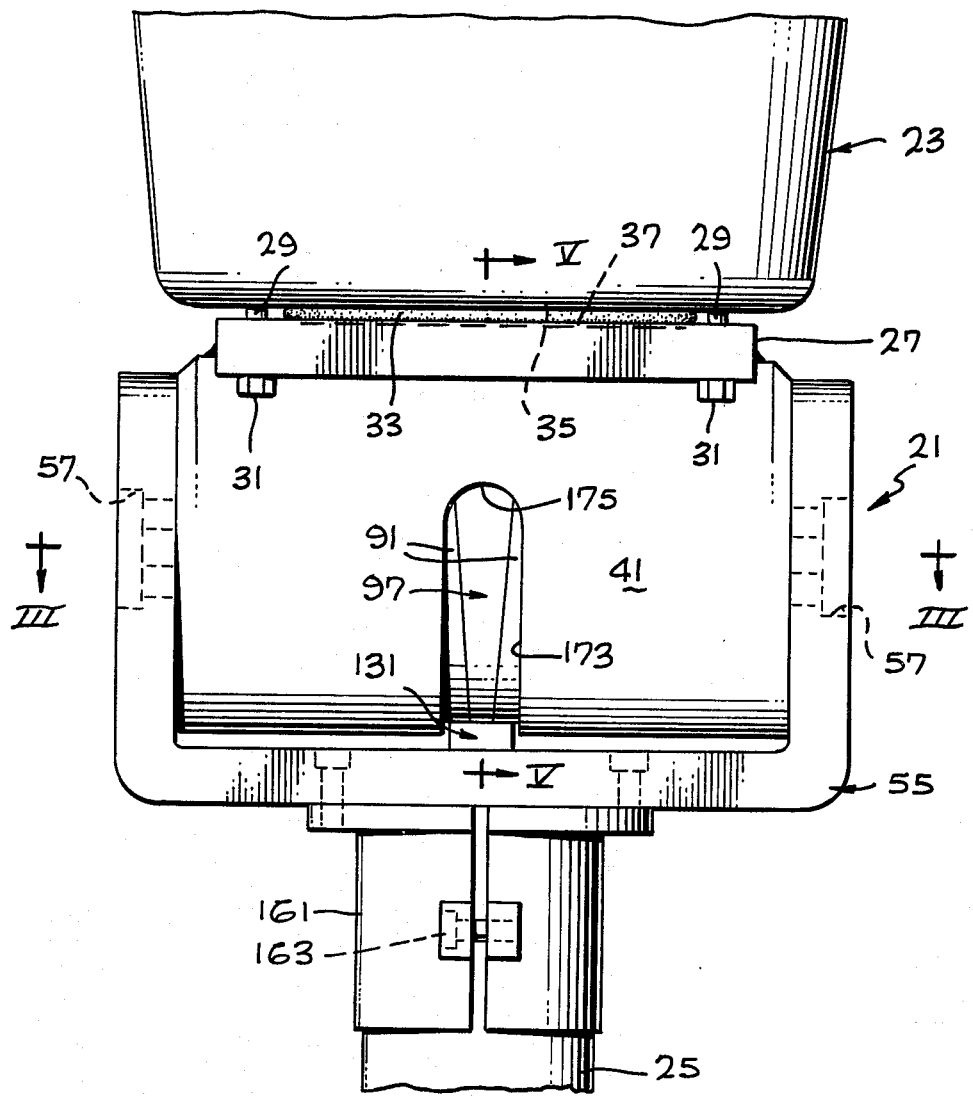
FIG. 1 comprises a front view of a prosthetic knee joint formed in accordance with the present invention.
Figure 2:
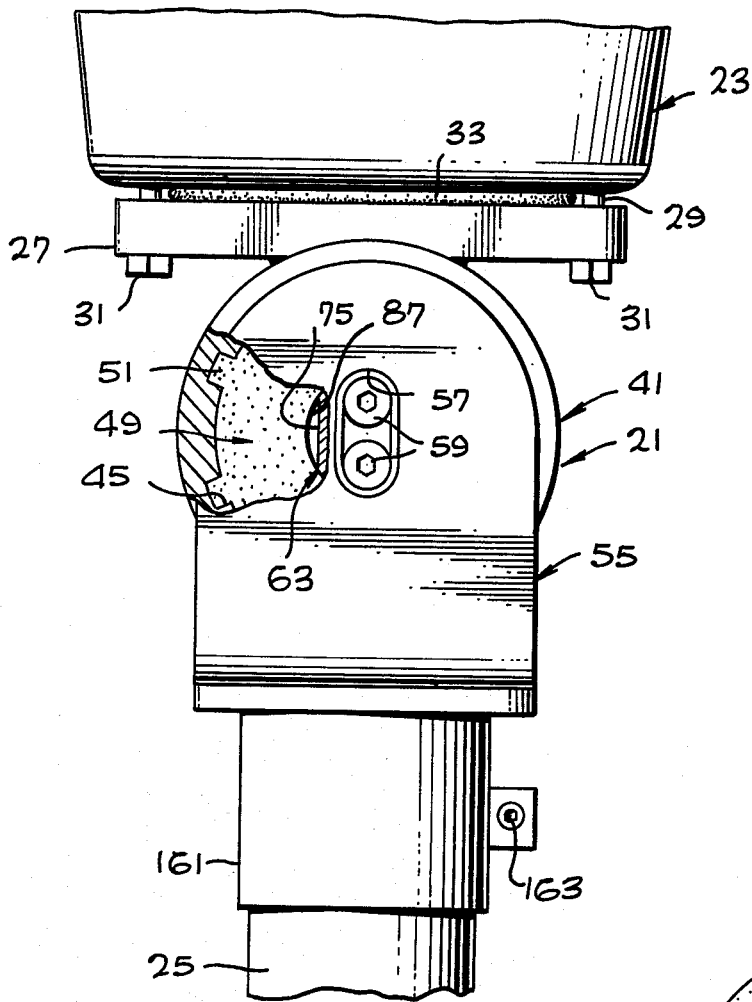
FIG. 2 comprises a side view of the structure illustrated in FIG. 1, partly in section.

Referring now to the drawings, and most particularly to FIGS. 1 and 2, there is shown a device which may employ the present invention, comprising a knee joint generally illustrated at 21 which may be connected to a stump-receiving cup or femural component 23 and a tibial or lower leg component 25.

At the lower end of the cup 23, a flange or plate 27 may be moveably attached by means of a plurality of stripper blots 29. Thus, the plate 27 can move toward and away from the cup 23, in a direction parallel to the axes of the stripper bolts 29, a distance determined by the dimensional relationship of the lower edge of the cup and the heads 31 of the bolts. In order to prevent the passage of dirt and foreign matter into the interior of the space between the plate 27 and the cup 23, and elastomeric "O" ring 33 may be positioned, as shown in FIG. 4, between an opposed pair of concave grooves 35 and 37 in the cup and plate, respectively. Thus, when the plate 27 moves relatively toward the cup 23, the "O" ring 33 will assume an oval cross section, as illustrated in FIG. 4. In other words, the concave grooves 35 and 37 will allow the "O" ring to spread out radially when the knee is locked as shown in FIG. 4, but will remain in contact with the bottom surfaces of the grooves when the joint is unlocked as shown in FIG. 2.

Figure 6:
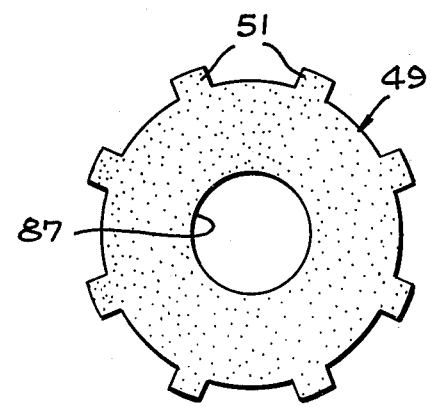
FIGS. 6 and 7 comprise axial views of brake discs which may be employed with the present invention.
Figure 5:
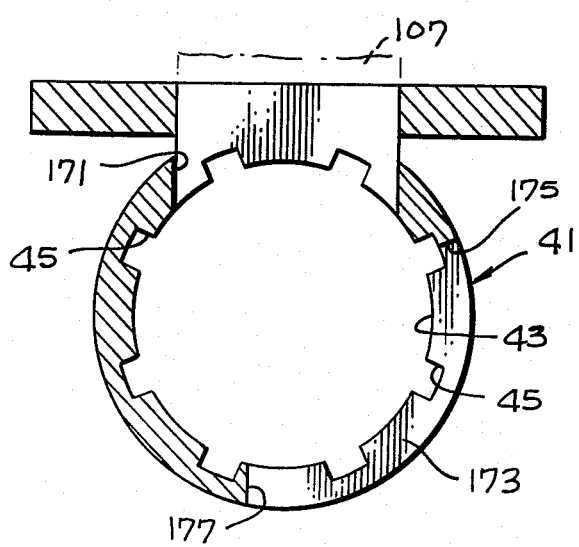
FIG. 5 comprises a sectional view of a housing which may be employed with the present invention, as seen along a line V—V in FIG. 1.

Referring now to FIG. 1, it can be seen that a housing 41 may be fixedly attached to the flange 27 by any suitable means, such as welding, etc. As shown in FIG. 5, the inner wall of the housing 41 may be provided with a bore 43 into which a plurality of spline-like parallel grooves 45 may be machined or otherwise suitably formed. Although eight such grooves 45 are illustrated, those skilled in the art will realize that any desired number of grooves may be provided and in any preferred locations. In fact, insofar as the scope of the present invention is concerned, as will be seen presently it is only necessary that some means be provided for prohibiting rotation relative to the housing 41 by a plurality of discs 49 (FIG. 6). As shown, each disc 49 may be provided with a number of radial extensions 51 equal to the number of grooves 45 in the internal wall of the housing. Again, any desired number of such radial extensions 51 could be provided, and at any desired positions. Alternatively, any structure may be employed which will prohibit relative movement between such discs and the housing.

As shown particularly in FIGS. 1 and 4, a substantially U-shaped yoke member 55 may be provided having an internal width, between the upright legs thereof, sufficient to fit closely adjacent the outer ends of the housing 41 as illustrated. The ends of the yoke 55 may be provided with suitable counterbore apertures 57 so that a plurality of machine screws 59 may be threaded into bores 61 in the opposite ends of a shaft 63 as illustrated in FIG. 4 (cf., FIGS. 11 and 12.)

In the ends of the housing 41 adjacent the sides of the yoke 55, suitable bearings 71 may be provided to allow easy, guided, rotational movement between the shaft and the housing. In other words, the shaft 63 and yoke 55 are thus supported for relative movement in the housing 41 by the bearings 71.

As shown particularly in FIGS. 11 and 12, the shaft 63 may have a circular peripheral surface 73, into which a pair of opposed, generally flat, longitudinal surfaces 75 may be formed for a purpose to be described presently.

Figure 3:
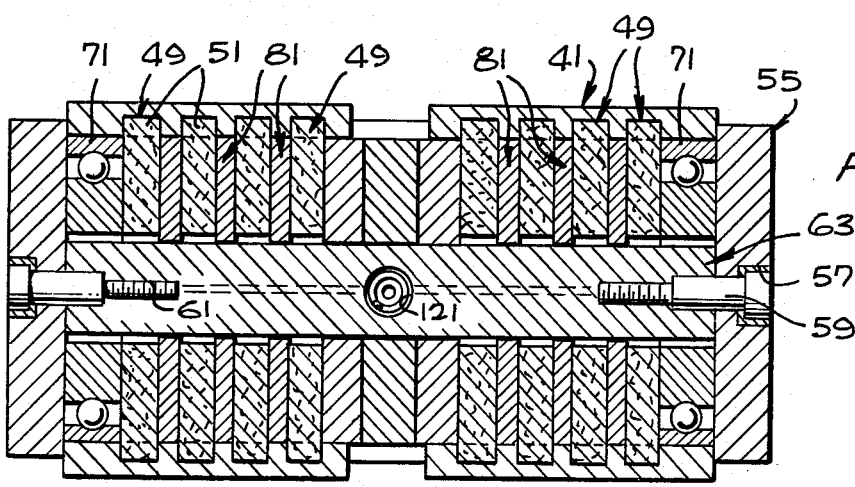
FIG. 3 comprises a sectional view of the knee joint shown in FIG. 1, as seen along a line III—III therein.
Figure 7:
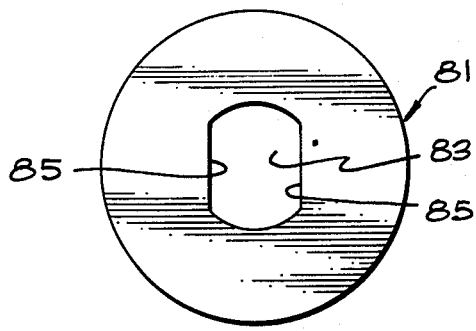

Referring again to FIGS. 3 and 4, it can be seen that the discs 49 may be mounted on the shaft 63 as illustrated. In the interspaces between discs 49, a plurality of discs 81 may be mounted. Generally, the discs 81 may be substantially flat, as are the preferred embodiments of discs 49, so that when the adjacent surfaces of the discs 49 and 81 are pushed together, friction will prevent them from rotating relative to one another. As illustrated in FIG. 7, each disc 81 may be provided with a central aperture 83 which generally conforms to the periphery of the shaft 63. In other words, the central bore of the washer-like discs 81 will preferably include a pair of flat edges 85 which can be aligned with the surfaces 75 of the shaft 63. Consequently, the discs 81 may be allowed to freely move along the axis of the shaft 63, but they are prevented from rotating relative thereto. Of course, any structure desired may be provided to prohibit or, at least, limit relative movement between the shaft 63 and the discs 81.

The discs 49, on the other hand, may be provided with a central bore 87 which corresponds to the circular periphery 73 of the shaft 63, thus allowing both axial and rotational relative movement between the discs 49 and the shaft. In the preferred embodiment illustrated here, the discs 49 are shown as being produced from any suitable fibrous material which may commonly be used in a brake. The discs 81, on the other hand, are illustrated as being of any desirable metalic or other element. Of course, the specific materials used to produce either or both of these disc elements should be considered to be within the design capabilities of one skilled in the art and the particular depictions are exemplary only.

In order to cause surface-to-surface abutment between each adjacent pair of discs, there may be provided a pair of reaction discs 91 (FUGS. 4 and 10), each having a flat surface 93 which may be located against, for example, a disc 49 a wedge surface 95. In axial elevation, the discs 91 may each resemble a disc 81, although a different configuration may be employed as will be discussed presently.

Figure 8:
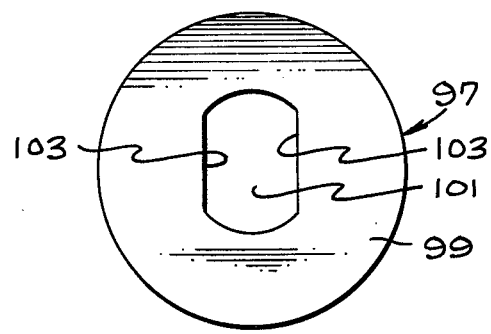
FIGS. 8 and 9 comprise axial and vertical elevation views, respectively, of a central actuating disc, having a double faced wedge configuration, which may be employed with the present invention.
Figure 9:
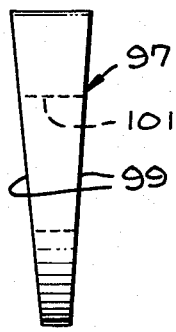
Figure 10:
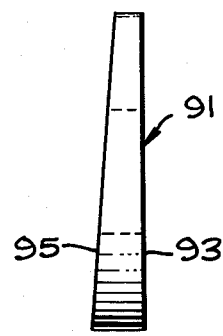
FIG. 10 comprises a vertical elevation view of a single faced wedge disc which may be employed with the present invention for actuation by the disc shown in FIGS. 8 and 9.

The discs 91 may be separated by a central or actuating disc 97 (FIG. 9) which may be provided with a pair of wedge surfaces 99, each of which may cooperate with the wedge surface 95 of a disc 91. As shown in FIG. 8, the central bore 101 of the disc 97 may resemble the central bore 83 of the discs 81, but may be provided with a pair of flat edges 103 which are slightly longer than the edges 85, thus allowing the central disc 97 to move diametrically, or abaxially, relative to the axis of shaft 63.

Figure 13:
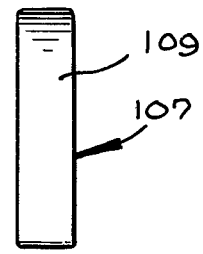
FIGS. 13 and 14 comprise end and side views respectively, of an actuating bar which may be employed with the present invention to provide for abaxial actuating movement of the actuating disc shown in FIGS. 8 and 9.
Figure 14:
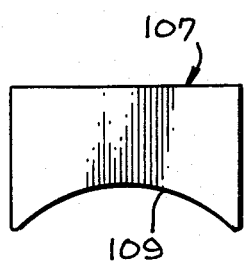

As shown in FIGS. 4, 13, and 14, the cup 23 may be provided with an actuator bar 107 having a curved actuating surface 109 for cooperation with the outer or peripheral edge of the central disc 97. As shown in FIG. 4, when the gap between the plate 27 and the cup 23 is closed, such as when the amputee's weight is imposed upon the cup, the actuator bar 107 will move through an aligned opening in the plate and push against the central disc 97, forcing it to move diametrically downwardly as seen in FIG. 4. When this occurs, the adjacent wedge or cam surfaces 99/95 force the reaction discs 91 to move axially along the shaft 63. As a result, the discs 49 and 81 may thus be moved into surface-to-surface frictional contact and rotation between adjacent discs will thus be prohibited. Since the discs 81 may be fixed against rotation relative to the shaft 63, while the discs 49 may be fixed against rotation relative to the housing 41, relative movement between the housing 41 and the shaft 63 will thus be prohibited. Consequently, the joint may thus be fully locked and the amputee will not fall as he stands up, takes a step, or rests on the prosthesis.

Figure 15:
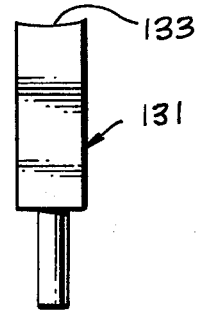
FIG. 15 comprises a side view of a portion of a biasing structure which may be employed to reverse the actuating movement of the central actuating disc.

When the force of the amputee's weight is withdrawn, the actuator bar 107 will be partially withdrawn through the aperture with which it is aligned in the plate 27, thus allowing the central actuator disc 97 to move diametrically in the opposite direction. In order to urge the disc 97 into the brake-released position shown in FIG. 1 from the brake-locked position shown in FIG. 4, the shaft 63 may be provided with a central blind- or partially through-bore 121, into which a spring 123 may be installed to bias a spherical bearing 125 against the upper, curved surface of the internal bore 101 in the central disc 97. Also, as shown in FIGS. 4 and 15, an actuator 131, having a surface 133 curved so as to cooperate with the outer periphery of the actuator disc 97, may be installed within an aperture 137 in the yoke 55. The actuator 131 may be provided with a shoulder 139, against which a spring 141 may act to bias the actuator in such a manner as to urge the central disc into the brake-released position.

In the illustrated embodiment, there is shown a fitting 145 which may be threadedly received within the aperture 137 of yoke 55. The fitting 145 may be provided with a longitudinal bore extending therethrough into which a machine or set screw 147 may be installed and threadedly received. Screw 147 may be turned for adjusting the biasing force exerted by the spring 141 as the screw is turned into or out of the bore within fitting 145. Of course, those skilled in the art will realize that the structure depicted for this purpose is simply one which is somewhat convenient from the standpoint of machining and engineering. Any structure which will allow the imposition of a motivational force on the disc 97 to release the brake may be utilized.

Similarly, those skilled in the art will realize that, if desired, discs 91 and 97 could be formed in such a manner as to be fixed relative to the housing instead of the shaft. In either case, structure such as the spring urged sphere 125 may be employed to initiate the brake-releasing movement of the central disc 97.

It will now be clear to those skilled in the art that it is unnecessary for the femoral and tibial components to be axially aligned; the knee joint may be locked in any position in which actuator bar 107 can move disc 97 diametrically. When the brake is released by removal of the amputee's weight on the joint, the pressure between the discs 49 and 81 will be relieved sufficiently enough to allow relative rotation. The yoke 55 may then be moved to a position such that the brake release actuators 125 and 131 exerts full force to move the disc 97 upwardly to its maximum extent, thus totally relieving the locking force.

The lower leg or tibial component 25 may be attached to the yoke 55 by any suitable means, such as a split clamp 161 which may be suitably attached to the yoke, for example, by machine screws 163. In this manner, when it is necessary to adjust the biasing force of spring 141, the lower leg element 25 can be temporarily removed to allow access to the screw 147.

If desired, the housing 41 may be formed as a single tubular element having a peripheral slot-opening 171 (FIG. 5) through which the bar 107 may extend to act upon the disc 97. Similarly, the housing may be provided with an elongated peripheral slot-opening 173 through which actuator 131 may extend. In this manner, abutment of the ends 175 and 177 of the slot 173 against actuator 131 may be employed to limit the amount of flexion of the joint 21 to that of a normal knee, i.e., about −6° to about +150°. Of course, any other structure may be employed to accomplish this function, as desired. Similarly, if desired, suitable spring or other biasing means may be used to normally align the femoral and tibial components to make the prosthesis act as much like a normal leg as possible.

Having now reviewed the above detailed description, those skilled in the art will realize that this invention relates to a very useful and novel knee joint and, particularly, to the structure for locking such a joint. They will also realize that any additionally desired structure, such a pivot stops, etc., may be employed to limit the rotational movement between the yoke 55 and the housing 41.

Those skilled in the art will also realize that a wide variety of embodiments may be designed in accordance with the present invention, many of which may not even resemble that depicted and described here but which, nevertheless, will fully employ the spirit and teachings of this invention as defined in the following claims. I claim:

1. A knee prosthesis comprising
 a femoral element including
  means for retaining an above-the-knee amputation stump,
  actuating means fixed to and extending from said retaining means, and
  a housing means mounted on said femoral element for reciprocatable movement between predetermined limits relative thereto, said housing means including
   slot means extending about a portion of the periphery of said housing and through which said actuating means extends and rotation prevention means in the interior surface of said housing;
a tibial element including
  shaft means pivotally supported in said housing for relative rotation therebetween about the axis of said shaft means and having
    rotation prevention means on the exterior surface of said shaft means and
  lower leg means fixedly attached to said shaft means; and
brake means for selectively preventing relative rotation between said housing and said shaft means comprising
  a plurality of first friction disc means mounted on said shaft means near the ends thereof for rotational and axial movement relative thereto and operatively engaged with said housing rotation prevention means,
  a plurality of second friction disc means mounted on said shaft means near the ends thereof for axial movement relative thereto and for rotational movement relative to said housing and operatively engaged with said shaft means rotation prevention means, said first and second disc means alternately arranged along the axis of said shaft means, and
  means for actuating said first and second discs into frictional facial engagement comprising
    a pair of reaction discs mounted on said shaft near the central portion of the length thereof, each reaction disc having
      a first surface generally parallel and adjacent to a facial surface of an adjacent one of said first and second discs and
      a second, cam surface oriented in a plane intersecting the facial plane of said first reaction disc surface, said reaction discs each located on said shaft means for axial movement relative thereto and operatively engaged with said shaft means rotation prevention means, and
    an actuation disc mounted on said shaft means in operative engagement with said shaft means rotation prevention means and abaxially movable relative to said shaft means, said actuation disc being located intermediate said reaction discs and adjacent the cam surfaces thereof and having
      cam surface means on the opposite surfaces thereof formed at complementary angles relative to said reaction disc cam surfaces, said actuation disc being located so as to be aligned with said slot means and the outer periphery thereof in contact with said actuating means.

2. The prosthesis of claim 1 wherein said actuation disc is wedge-shaped in cross section, thus exerting an axial, friction generating force against said reaction discs when said actuation disc is moved abaxially relative to said shaft means by said actuating means in a first direction and withdraws such force when moved abaxially in the opposite direction.

3. A knee prosthesis comprising
a femoral component,
a tibial component pivotally connected to said femoral component, and
a selectively actuatable brake means interconnecting said femoral and tibial components to prohibit pivotal movement therebetween when a generally vertical downward force is exerted upon said femoral component comprising
  a housing fixedly attached to one of said components and having
    rotation prevention means therein and
    slot means extending through a wall of said housing along a portion of the circumferential periphery thereof generally equidistant from the axial ends of said housing component,
  a shaft, rotatably mounted for movement about its axis, within said housing and fixedly attached to the other of said components and having
    rotation prevention means thereon and
    means for exerting a substantially abaxially directed biasing force located generally in alignment with said slot means,
  a set of interleaved brake disc means, each disc arranged in facial relationship to an adjacent brake disc means, on each end of said shaft, and
  every second one of said brake disc means in cooperative relationship with one of said rotation prevention means and the intermediate ones of said brake disc means in cooperative relationship with the other of said rotation prevention means, and
  means for actuating said sets of brake disc means toward the opposite ends of said shaft and into frictional facial contact with one another to prevent pivotal movement between said components comprising
    an actuation disc mounted on said shaft in operative relationship with said shaft rotation prevention means, generally aligned with said slot means and said biasing force exerting means, abaxially movable relative to said shaft, and having a pair of cam faces on the opposite sides thereof extending along planes which intersect the axis of said shaft at angles other than 90°,
    a pair of reaction discs on said shaft means, one on either side of said actuation disc in operative relationship with said shaft rotation prevention means, each reaction disc having
      a first face located adjacent and generally parallel to one of said brake discs and
      a second face adjacent to one of said actuation disc cam faces and formed at an angle complementary to said cam face, and
    means fixed to one of said components and extending through said slot means and into contact with said actuation disc for selectively exerting a braking force upon said actuation disc in opposition to a force constantly exerted on said actuation disc by said biasing force exerting means such that pivotal movement can occur when the biasing force is larger than such braking force and pivotal movement cannot occur when the braking force is larger than the biasing force.

* * * * *